United States Patent
Keene et al.

(10) Patent No.: US 10,076,319 B2
(45) Date of Patent: Sep. 18, 2018

(54) ADAPTIVE DEVICES AND METHODS FOR ENDOSCOPIC WOUND CLOSURES

(71) Applicant: Biolife, L.L.C., Sarasota, FL (US)

(72) Inventors: Talmadge Kelly Keene, Ruskin, FL (US); John Tifton Fordham, Indialantic, FL (US); Louis M. Guzzi, Longwood, FL (US); Charles E. Entenmann, Key Largo, FL (US)

(73) Assignee: BIOLIFE, L.L.C., Sarasota, FL (US)

(*) Notice: Subject to any disclaimer, the term of this patent is extended or adjusted under 35 U.S.C. 154(b) by 0 days.

(21) Appl. No.: 15/022,281

(22) PCT Filed: Sep. 17, 2014

(86) PCT No.: PCT/US2014/056011
§ 371 (c)(1),
(2) Date: Mar. 16, 2016

(87) PCT Pub. No.: WO2015/042104
PCT Pub. Date: Mar. 26, 2015

(65) Prior Publication Data
US 2016/0220239 A1   Aug. 4, 2016

Related U.S. Application Data

(60) Provisional application No. 61/878,677, filed on Sep. 17, 2013.

(51) Int. Cl.
*A61B 17/08* (2006.01)
*A61B 17/00* (2006.01)
(Continued)

(52) U.S. Cl.
CPC ........ *A61B 17/00491* (2013.01); *A61B 10/04* (2013.01); *A61B 17/0057* (2013.01);
(Continued)

(58) Field of Classification Search
CPC ...... A61B 17/0057; A61B 2017/00575; A61B 2017/00579; A61B 2017/00584;
(Continued)

(56) References Cited

U.S. PATENT DOCUMENTS 2,847,997 A * 8/1958 Tibone ............. A61B 17/12104
                                                        604/104
4,364,377 A * 12/1982 Smith .................... A61B 17/12
                                                        600/12
(Continued)

FOREIGN PATENT DOCUMENTS

WO   WO 2012061193 A2 *  5/2012  .......... A61K 9/5094
WO   WO 2013040080 A1 *  3/2013  ............ A61L 15/14

OTHER PUBLICATIONS

Magnetite. (n.d.). Dictionary.com Unabridged. Retrieved Jul. 20, 2016 from Dictionary.com website http://www.dictionary.com/browse/magnetite.*
(Continued)

*Primary Examiner* — Katrina Stransky
*Assistant Examiner* — Kankindi Rwego
(74) *Attorney, Agent, or Firm* — Charles J. Prescott, P.A.

(57) ABSTRACT

This invention is directed to devices and methods for improving wound closures produced during endoscopic surgery. These methods are directed to delivering and applying a quantity of hemostatic agents in either powder, solid, liquid, or gel form onto an open wound produced e.g., by polyp removal, followed by the application of pressure. The method is implemented preferably using existing endoscopic equipment; however, modifications to existing endoscopic insertion tubes, application and tamping devices and endoscopic clips deployed from the distal end of the insertion tube during endoscopic surgery are also within the scope of this invention.

5 Claims, 21 Drawing Sheets

(51) Int. Cl.
*A61B 10/04* (2006.01)
*A61B 17/04* (2006.01)
*A61B 17/22* (2006.01)
*A61B 90/00* (2016.01)
*A61B 90/30* (2016.01)

(52) U.S. Cl.
CPC ....... *A61B 90/361* (2016.02); *A61B 2017/003* (2013.01); *A61B 2017/0065* (2013.01); *A61B 2017/00296* (2013.01); *A61B 2017/00522* (2013.01); *A61B 2017/00544* (2013.01); *A61B 2017/00579* (2013.01); *A61B 2017/00623* (2013.01); *A61B 2017/00659* (2013.01); *A61B 2017/00668* (2013.01); *A61B 2017/00676* (2013.01); *A61B 2017/00685* (2013.01); *A61B 2017/00876* (2013.01); *A61B 2017/0417* (2013.01); *A61B 2017/22067* (2013.01); *A61B 2090/306* (2016.02)

(58) Field of Classification Search
CPC ........... A61B 2017/00588; A61B 2017/00592; A61B 2017/00597; A61B 2017/00601; A61B 2017/00606; A61B 2017/0061; A61B 2017/00615; A61B 2017/00619; A61B 2017/00623; A61B 2017/00628; A61B 2017/00632; A61B 2017/00637; A61B 2017/00641; A61B 2017/00646; A61B 2017/0065; A61B 2017/00654; A61B 2017/00659; A61B 2017/00663; A61B 2017/00668; A61B 2017/00672; A61B 2017/00676; A61B 1/00; A61B 1/0008; A61B 1/00082; A61B 1/00087; A61B 1/00089; A61B 1/00091; A61B 1/00094; A61B 1/00096; A61B 1/00098; A61B 1/00101; A61B 1/00103; A61B 17/12; A61B 17/1209; A61B 17/12013; A61B 17/12022; A61B 17/12027; A61B 17/12031; A61B 17/12036; A61B 17/1204; A61B 17/12045; A61B 17/12099; A61B 17/12104; A61B 17/12109; A61B 17/12113; A61B 17/12118; A61B 17/12122; A61B 2017/12004; A61B 2017/12018; A61B 2017/1205; A61B 2017/12054; A61B 2017/12059; A61B 2017/12063; A61B 2017/12068; A61B 2017/12072; A61B 2017/12077; A61B 2017/12081; A61B 2017/12089; A61B 2017/1209; A61B 2017/12095; A61L 24/00; A61L 27/04; A61L 27/042; A61K 33/26; A61K 9/5094

See application file for complete search history.

(56) References Cited

U.S. PATENT DOCUMENTS

| | | | |
|---|---|---|---|
| 6,187,347 B1 | 2/2001 | Patterson et al. | |
| 6,296,604 B1* | 10/2001 | Garibaldi | A61B 17/12022 600/12 |
| 6,596,791 B2* | 7/2003 | Santar | A61K 8/65 524/35 |
| 7,249,604 B1* | 7/2007 | Mohanraj | A61B 17/12022 128/898 |
| 8,012,454 B2* | 9/2011 | Rioux | A61K 9/0009 424/1.11 |
| 2003/0216729 A1 | 11/2003 | Marchitto et al. | |
| 2008/0177213 A1* | 7/2008 | Kohler | A61L 15/60 602/48 |
| 2010/0087854 A1 | 4/2010 | Stopek et al. | |
| 2011/0060295 A1* | 3/2011 | Hen | A61K 9/0014 604/290 |
| 2011/0178495 A1 | 7/2011 | Ji | |
| 2012/0065674 A1* | 3/2012 | Levy | A61B 17/0057 606/214 |

OTHER PUBLICATIONS

Glick JB, Kaur RR, Siegel D. Achieving hemostasis in dermatology—Part II: Topical hemostatic agents. Indian Dermatol Online J 2013; 4:172-6.*

* cited by examiner

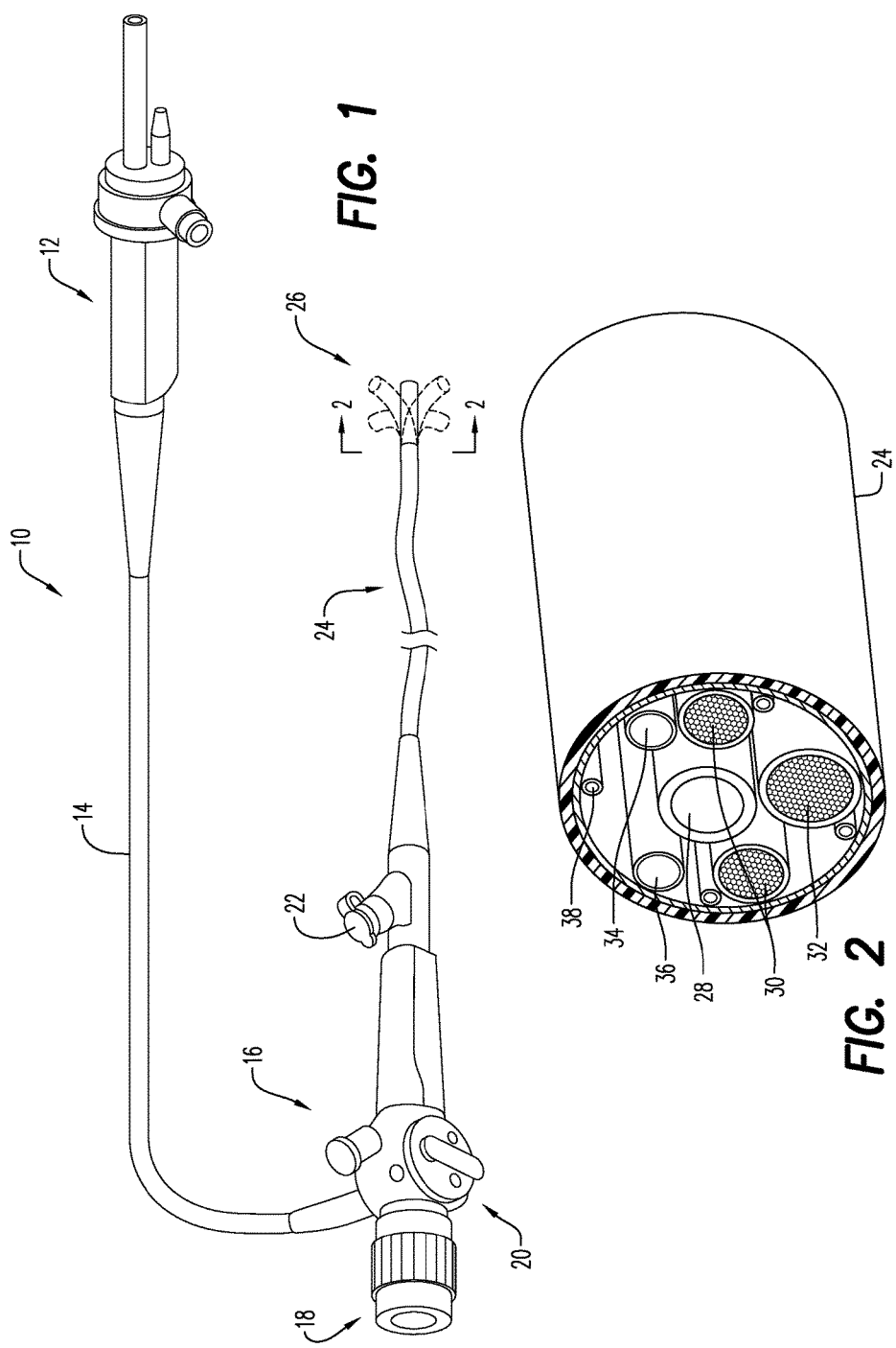

ADAPTIVE DEVICES AND METHODS FOR ENDOSCOPIC WOUND CLOSURES

CROSS-REFERENCE TO RELATED APPLICATIONS

Not applicable

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

Field of the Invention

This invention is directed to a method for improving wound closures during endoscopic surgery after polyp removal and biopsy samples are taken. More specifically, this disclosure is directed to applying a quantity of resin ferrate or other hemostatic substances in either powder, solid, liquid or gel form onto an open wound, followed by the application of pressure. The methods are implemented preferably using existing endoscopic equipment; however, modifications to existing endoscopic insertion tubes and adaptive devices are also within the scope of this invention. The wound may be located in the alimentary tract or other serosal mucosa, accessed for endoscopic treatment through a natural orifice of the body.

Description of Related Art

Endoscopy is the medical science of looking inside or typically within the body for medical reasons using an endoscope. An endoscope is an instrument used to examine the interior of a hollow organ or cavity of the body. Unlike most other medical imaging devices, endoscopes are inserted directly into the organ.

An endoscope typically includes a rigid or flexible tube, a light delivery system to illuminate the organ. The light source is typically being positioned outside the body, the light being directed typically by an optical fiber system to illuminate the interior organ. The endoscope also includes a lens system for transmitting the image from the objective lens to the viewer, and an eyepiece. Additional channels are provided to allow entry of medical instruments and manipulators.

A healthcare provider may use an endoscope for any of a plurality of purposes, including investigation of symptoms such as symptoms in the digestive system including nausea, vomiting, abnormal pain, difficulty swallowing, and gastrointestinal bleeding. The endoscope may also be used to confirm a diagnosis, most commonly by performing a biopsy, to check for conditions such as anemia, bleeding, inflammation, and cancers of the digestive system. Treatment may also be administered by an endoscope such as cauterization of a bleeding vessel, the widening of a narrow esophagus, cutting off of a polyp or removing a foreign object within the organ.

One particularly useful application of the endoscope is the removal of polyps and other growths within the interior walls of the organ under examination. However, the techniques for removing the polyp include typically either a cutting device or a heated loop device, both of which leave a wound at the base of the polyp which typically bleeds profusely. To arrest the blood flow from the incision, surgical clamps are the most preferable means of arresting that blood flow. A plurality of these small surgical clamps is attached around and across the wound so as to effect a wound closure. However, these clamps are difficult to apply, are small and unable to approximate wide wounds, and do not often effect a complete wound closure leaving some bleeding. Moreover, the clamps must be left in place for a time sufficient to arrest bleeding, after which they are eventually eliminated by normal bowel movement in the colon or intestine.

Another means for arresting blood flow from a wound of this nature is to simply spray a powder starch-like material onto the wound until it is sufficiently covered to absorb the blood flow and cause the cessation of blood flow from that wound. However, due to a lack of containment of this powder, a large quantity of this material is required to effect bleeding cessation, leaving a substantially greater amount of material than typically needed if applied directly to the wound from an exposed wound.

The present invention provides a method of wound closure after a polyp or removal during endoscopic surgery and the like. This method is directed to applying a quantity of a hemostatic substance in either powder, solid, liquid, or gel form onto the open wound followed by the application of pressure. Various adaptive devices are provided to accomplish both the deployment of the hemostatic substance onto the wound and the application of pressure thereagainst to effect complete hemostasis.

The foregoing examples of the related art and limitations related therewith are intended to be illustrative and not exclusive. Other limitations of the related art will become apparent to those skilled in the art upon a reading of the specification and a study of the drawings.

BRIEF SUMMARY OF THE INVENTION

This invention is directed to a method for improving wound closures after polyp removal during endoscopic surgery. This method is directed to applying a quantity of a hemostatic substance e.g., resin ferrate in either powder, solid, liquid, or gel form onto an open wound produced by polyp removal followed by the application of pressure. The method is implemented preferably using existing endoscopic equipment, however, modifications to existing endoscopic insertion tubes is also within the scope of this invention.

Powder form of Hemostatic Substance

Using the powder or granular form of the resin ferrate or other granular or particulate hemostatic substance, this material may be delivered through the central channel of an endoscope by air pressure, by plunger, by a screw feed, by gravity, or by a liquid carrier. To direct and apply pressure against the resin ferrate powder, several devices may be employed. For example, a flexible bowl or funnel formed of thin resilient material deployed against and covering the wound. Powder directed into the bowl or funnel is then pressed against the wound. When the powder is combined with magnetite, thin magnetic wires deployed from the distal end of the endoscope will capture the magnetic powder, after which the magnetic wires are directed against the wound for a time sufficient for the powder to become affixed onto the open wound. Other powder deployment and pressure application devices are also disclosed.

Tablet/Solid Form of Hemostatic Substance

Several embodiments of this disclosure utilize a solid or compressed powder device for deployment onto the wound. One embodiment is in the form of a donut-shaped disc which is held within the end of the insertion tube and provides viewing access by the camera within the insertion tube. The camera thus provides accurate placement of the disc over the wound site.

In another embodiment, a solid disc is temporarily bonded or adhered on the side of the bleeding tip providing guided positioning and pressure of the disc against the wound site for a time sufficient to adhere the disc to the wound site.

Mini-sized solid tablets which slidably translate within a delivery tube are delivered sequentially onto the wound site. The column of tablets may be pushed by a plunger or connected by an elongated suture and pulled from the end of the bending tip. The hemostatic substance forming the disc may include magnetite which may be manipulated and applied by a magnet.

Motive Force

A number of means for moving the hemostatic powder or solid tablets along the hollow interior of a delivery tube within the insertion tube may be employed, namely, a plunger, gas or air pressure, a venture, and various forms of augers or feed screws.

The following embodiments and aspects thereof are described and illustrated in conjunction with systems, tools and methods which are meant to be exemplary and illustrative and not limiting in scope. In various embodiments one or more of the above-described problems have been reduced or eliminated while other embodiments are directed to other improvements. In addition to the exemplary aspects and embodiments described above, further aspects and embodiments will become apparent by reference to the drawings and by study of the following descriptions.

BRIEF DESCRIPTION OF THE SEVERAL VIEWS OF THE DRAWING(S)

FIG. 1 is a pictorial view of a typical endoscope assembly.

FIG. 2 is a section view in the direction of arrows 2-2 in FIG. 1.

Figure 29:
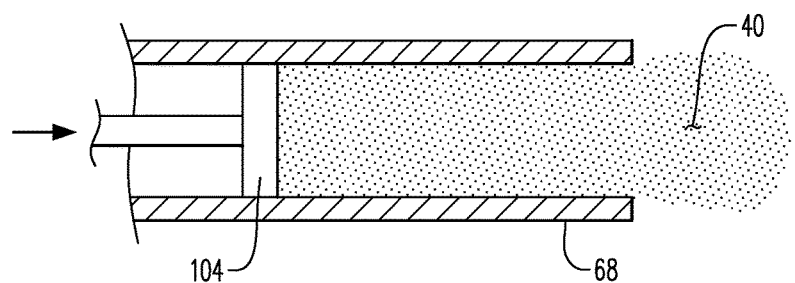
Figure 30:
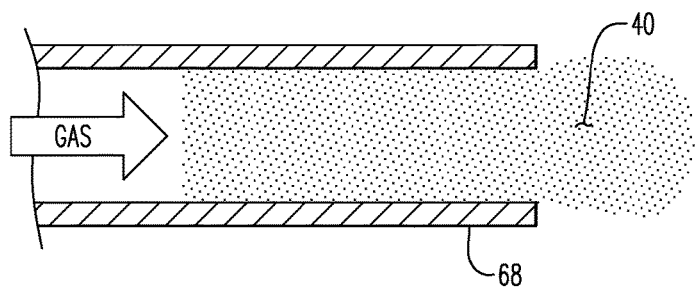
Figure 31:
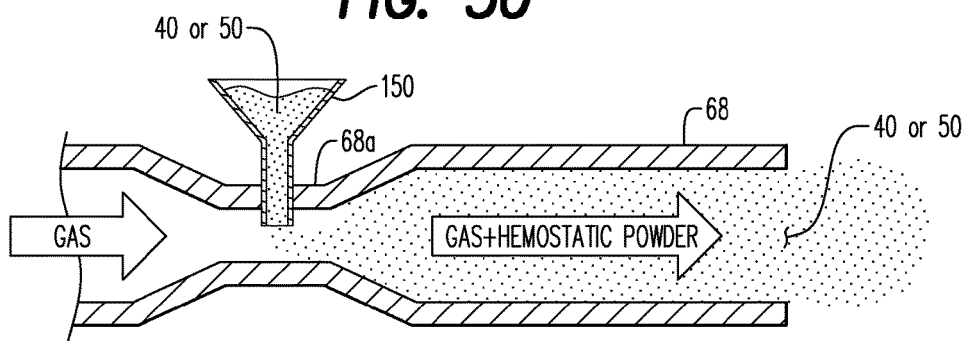
Figure 32:
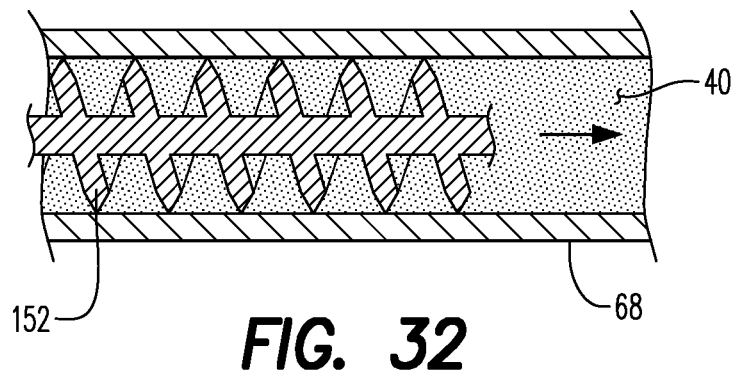
Figure 33:
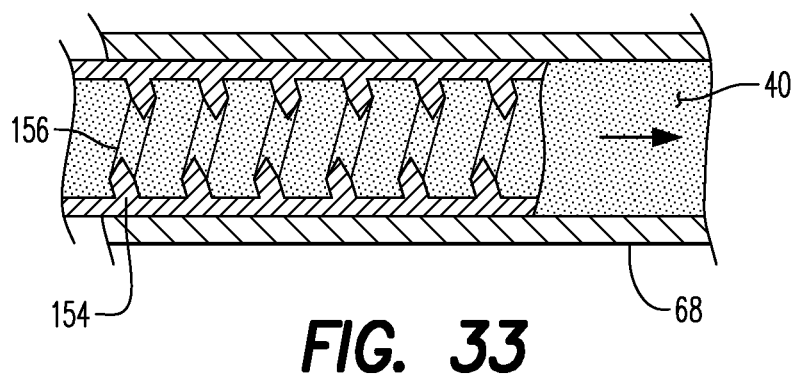
Figure 34:
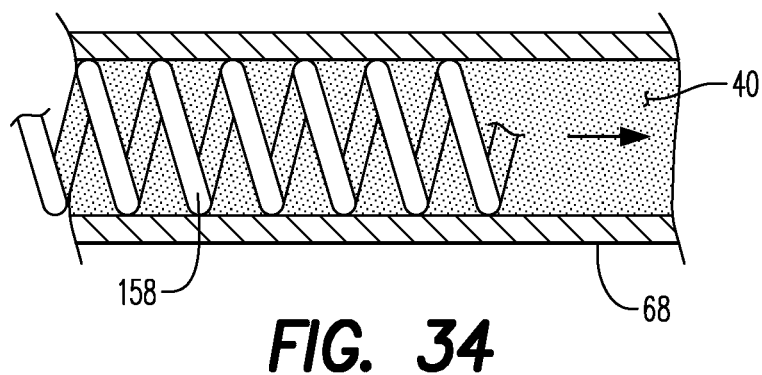

FIGS. 29 to 34 show a number of embodiments of means for delivering the hemostatic powder or solid pellets through the insertion tube and bending tip. In FIG. 29, a plunger is utilized while in FIG. 30, gas under pressure forces the hemostatic powder for discharge through the bending tip. In FIG. 31, a venturi is utilized to draw the hemostatic powder into the venturi for discharge under gas pressure from the end of the bending tip. FIG. 32 shows a drill auger utilized to force the hemostatic powder or solid pellets through the insertion tube. FIG. 33, shows the utilization of an outer auger to force the hemostatic powder or solid pellets through the insertion tube. FIG. 34 discloses a wire auger for the same purpose.

Exemplary embodiments are illustrated in reference figures of the drawings. It is intended that the embodiments and figures disclosed herein are to be considered to be illustrative rather than limiting.

DETAILED DESCRIPTION OF THE INVENTION

Nomenclature 10. endoscopic assembly
12. light guide connector
14. universal cord
16. endoscope head
18. eyepiece
20. controls
22. biopsy port
24. insertion tube
26. bending tip
28. biopsy suction channel
30. fiber optic light guides
32. fiber optic image bundle
34. water tube
36. air tube
38. tip bending control wires
40. hemostatic powder
42. flexible bowl
44. funnel shaped bowl
46. magnetic arm bowl
48. elastic ring
50. hemostatic powder with magnetite
52. barbed bowl
54. inflatable balloon
56. balloon tamponade
58. magnet
60. balloon
62. stent
64. application catheter
66. clear cap
68. application catheter
68a. venturi
70. magnet
72. $FE^{+3}$ spray
74. spray nozzle
76. endoclip
78. resilient wire jaws
80. insertion tool
82. magnetized barrel
84. styptic powder
86. hemostatic tablet
88. hemostatic tablet
90. camera
92. hemostatic tablet
100. wound covering
102. hemostatic powder with magnets and magnetite
104. plunger
106. hemostatic tablets
108. suture
110. barbed magnets
112. barb
114. barbed anchor
116. barb
118. barbed anchor
120. barb
122. wire
124. hemostatic powder coated sheet
130. hemostatic powder distribution head assembly
132. distribution head
134. apertures
140. spring wire clip
142. spring wire
144. barbs
146. pivot anchor
148. push/pull wire
150. funnel
152. drive auger
154. outer auger
156. central feed passage
158. wire auger As referenced herein, the term "hemostatic powder" is preferably WOUNDSEAL powder, a resin/ferrate or hydrogen resin as taught in U.S. Pat. No. 6,187,347 which produces or forms a scab or protective coating over the wound. The term "hemostatic tablet or solid" is preferably STATSEAL, refers to a compressed form of WOUNDSEAL powder. The term "intestine" is used to designate the alimentary tract or other serosal mucosa.

Referring now to FIGS. 1 and 2, an endoscope assembly is shown generally at numeral 10 and includes an endoscope head 16 having an eye piece 18 and controls 20 thereon. The endoscope assembly 10 also includes a side insertion biopsy port 22 which leads to an elongated insertion tube 24. Connected to the side of the eyepiece 16 is an elongated flexible inward cord 14 having a light guide connector 12 disposed at the distal end of universal cord 14.

In well known fashion, the insertion tube 24 houses a biopsy suction channel 28, fiber optic light guides 30, a fiber optic image bundle 32, a water tube 34, an air tube 36, and a plurality of evenly spaced tip bending control wires 38. These control wires 38 are controllably actuated to bend the bending tip 26 in any desired direction as seen in FIG. 1. The endoscopic assembly 10 is the working tube that is inserted through an endoscope. The insertion tube 24 may pass directly through the endoscope head 16 or may be covered with a sheath to protect the hemostatic substance. Both sheath and tube pass through the endoscope head 16.

Figure 3:
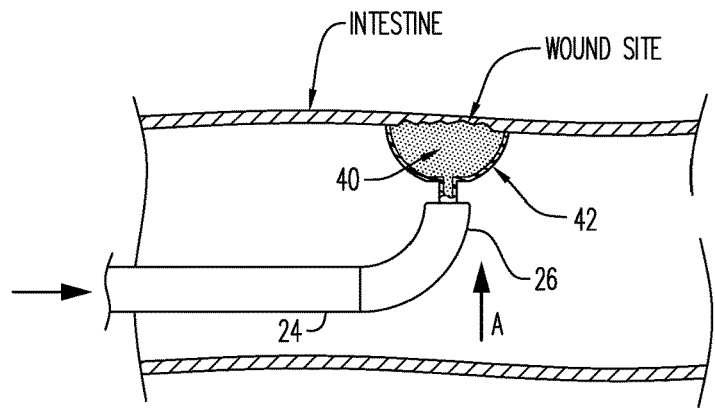
FIG. 3 is a schematic section view of the deployment of one embodiment of the invention by applying a quantity of a hemostatic powder over a wound site within an intestine.

FIGS. 3 to 11 depict expandable devices which are deployed in collapsed form through the insertion tube 24 and then automatically expand when exiting the bending tip 26. FIG. 3 shows a flexibly expandable bowl 42 applied over the wound after bending tip 26 as shown. Hemostatic powder 40 is forced through the insertion tube 24 into the bowl 42. The bowl 42 is then compressed in the direction of arrow A to apply pressure to the wound to press the powder 40 into contact with the wound to stop bleeding. The bowl 42 may have a rigid bottom with flexible sides that move in accordion fashion. The sides of the bowl 42 may flex outwards allowing pressure to be applied. The entire bowl 42 may be flexible.

Figure 4:
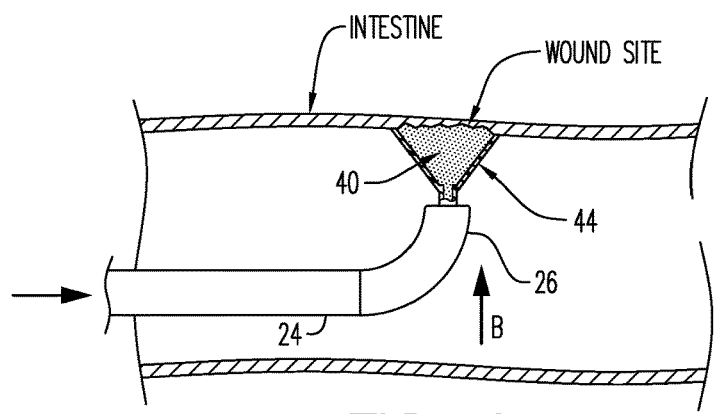
FIG. 4 is a schematic section view of another embodiment of the invention showing deployment of a quantity of a hemostatic substance powder over a wound site within an intestine.

In FIG. 4, a flexibly expandable funnel shaped bowl 44 is applied over the wound and hemostatic powder 40 is forced through the insertion tube 24 into the bowl 44 which is then compressed to apply pressure to press the powder 40 into contact with the wound to stop bleeding. The bowl 44 may have a rigid bottom with flexible sides that accordion. The sides of the bowl 44 may flex outwards allowing pressure to be applied.

Figure 5:
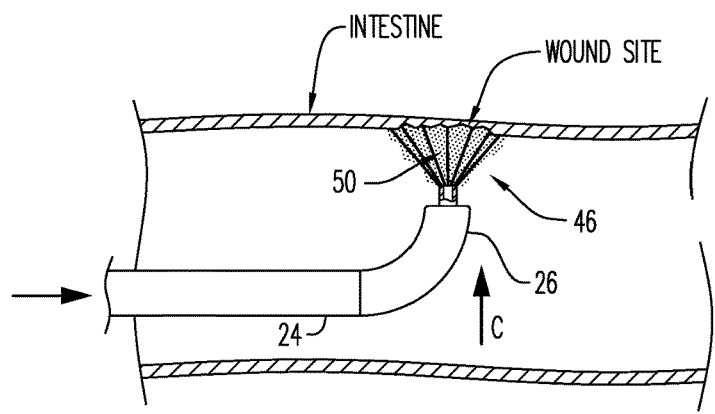
FIG. 5 is a schematic section view of another embodiment of the invention deploying a quantity of a hemostatic powder over a wound site of an intestine.

FIG. 5 shows an expandable magnetic arm bowl 46 in combination with hemostatic powder with magnetite 50 which is held within the magnetic bowl 46 to facilitate application against the wound. The magnetic bowl 46 may be deployed with the hemostatic powder 50 attached prior to application or forced through the insertion tube 24 after deployment.

Figure 6A:
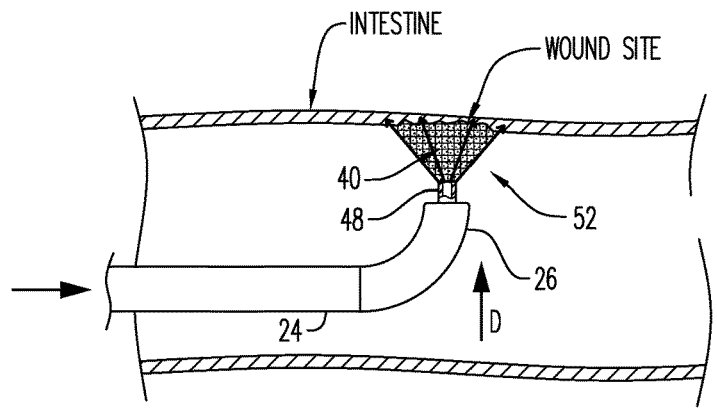
FIGS. 6A, 6B and 6C are schematic section views of another embodiment of the invention showing placement of a quantity of a hemostatic powder over a wound site within an intestine.
Figure 6B:
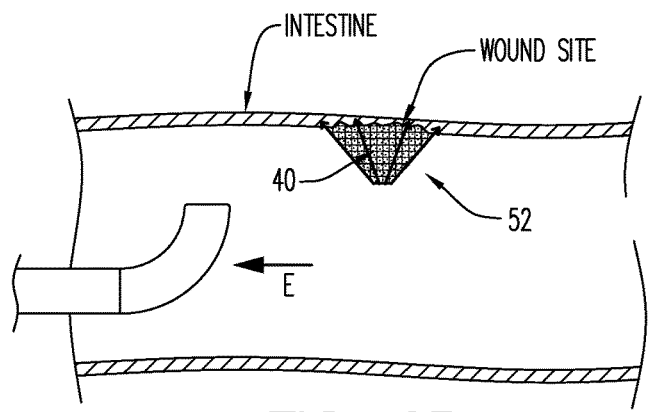
Figure 6C:
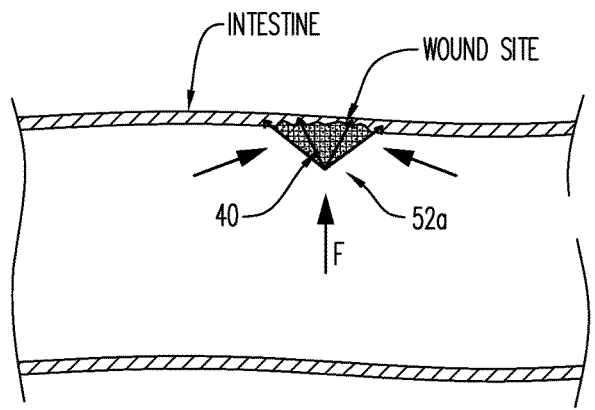

In FIGS. 6A, 6B and 6C, a barbed expandable netted bowl 52 includes barbed end points which are designed to penetrate the tissue and hold the bowl 52 in place when forced in the direction of D. The bowl 52 is then filled with hemostatic powder 40, after which the following actions may take place in any order. The bowl 52 closes, detaches from the bending tip 26, and then collapses. The collapsing of the bowl 52, forces the hemostatic powder 40 onto the wound, while slightly approximating the wound.

In one embodiment, the sides of the bowl 52 may be elastic, and there may be an elastic ring 48 at the end of the insertion tube as seen in FIG. 6A. The bowl 52 is attached to the intestine around the wound which is then filled with powder. There are wires attached to the barbs to keep the bowl 52 open during filling and open for attachment. After attachment of the barbs and removal of the insertion tube 24 in FIG. 6B, the wires pull from the barbs, and the elastic net plunger collapses about itself in all directions, closing and applying pressure on the hemostatic powder 40 against the wound approximating the wound. The bowl 52 remains at the wound site.

In another embodiment, the arms of the bowl 52 are made of wire. The bowl 52 is attached and filled with powder as previously described, after which the insertion tube 24 is rotated whereupon the wires wrap around themselves, closing the bowl 52, applying pressure on the hemostatic powder 40 against the wound, approximating the wound. The rotation then shears the wires, leaving the bowl 52 connected to the wound site.

In another embodiment, the arms of bowl 52 are made of wire. The bowl 52 is deployed and attached around the wound after which the bowl 52 is filled with powder 40 and then retracted into the bending tip 26. Applying pressure to the powder against the wound approximates the wound. The locking ring 48 closes the small end of the bowl 52, and the wires are cut/broken closing the bowl 52 and leaving it in place.

In another embodiment after attachment and fill of the bowl 52 the bowl 52 may be crushed, holding its crushed shape. The crushing applies pressure to the hemostatic powder 40 on the wound. This design would not approximate the wound.

In further embodiments, an outer bowl 52 may be used to hold an inner collapsible netting in place until it can be deployed and filled with hemostatic powder 40. The bowl 52 may also be magnetized to allow it to hold a magnetic hemostat 50. The bowl 52 could be filled with hemostatic powder 50 prior to adhering to the intestine walls. The bowl 52 may also be adhered to means other than barbed points. The barbed points may be made from biosorbable materials, metal, or plastic.

Figure 7:
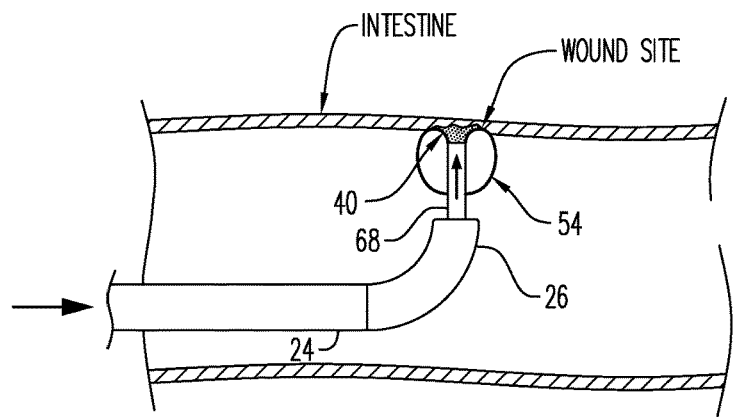
FIG. 7 is a schematic section view of another embodiment of the invention being deployed to place a quantity of a hemostatic powder over a wound site within an intestine.

In FIG. 7, an inflatably expandable balloon 54 is employed to both contain the hemostatic powder 40 and to apply pressure via mechanical force (pushing the tube) on further inflation of the balloon. An application catheter 68 is extendable from the bending tip to deliver the hemostatic powder 40 to the wound site. The balloon 54 may be designed to create a funnel at low pressure and create a flatter surface with increased pressure against the wound site.

Figure 8A:
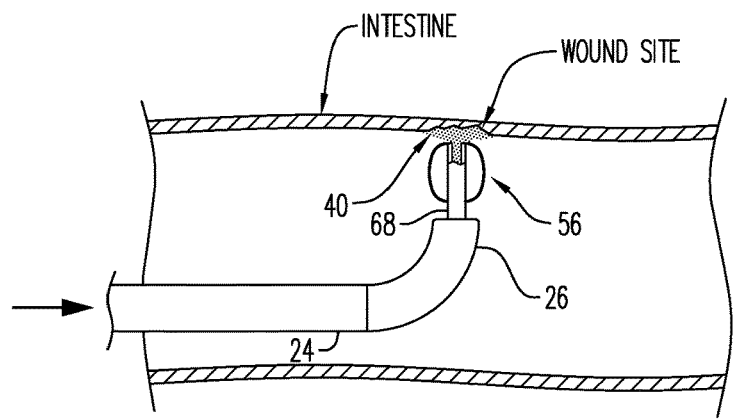
FIGS. 8A and 8B are schematic section views showing the deployment of another embodiment of the invention utilizing a balloon tamponade to place and press hemostatic powder against a wound site.
Figure 8B:
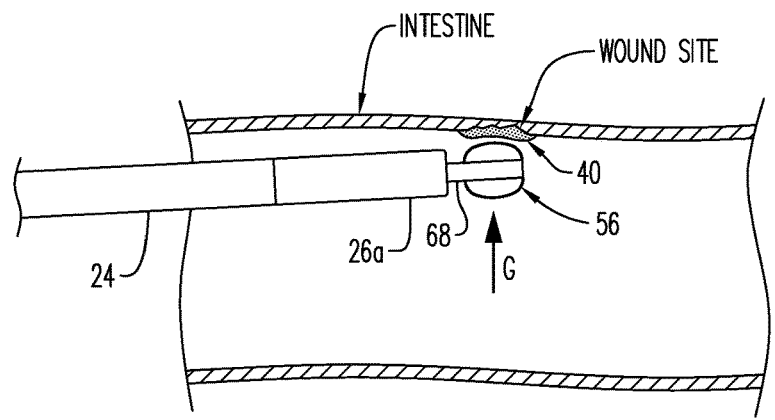

FIGS. 8A and 8B disclose an expandable balloon tamponade 56 to place and press the hemostatic powder 40 against a wound site. The balloon tamponade 56 contains the hemostatic powder around the wound site, after which the side is used as a tamponade to apply pressure to the wound in the direction of arrow G in FIG. 8B.

Figure 9:
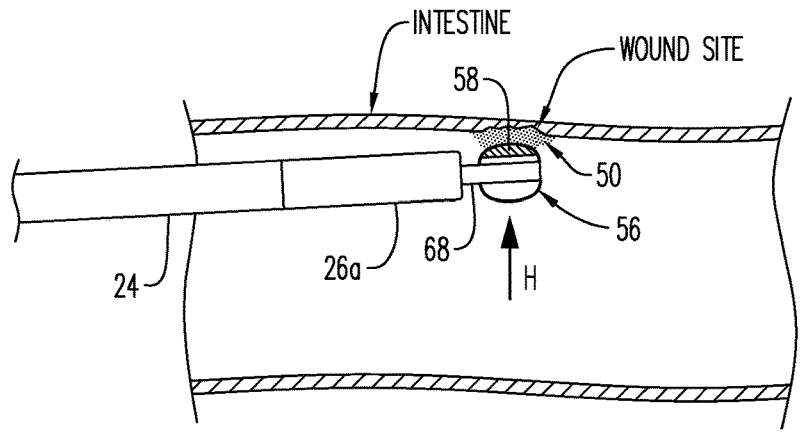
FIG. 9 is a schematic section view of another embodiment of the invention incorporating a balloon tamponade with an internal magnet to deploy and compress hemostatic powder containing magnetite against a wound site.

FIG. 9 incorporates the expandable balloon tamponade 56 with an internal magnet 58 to deploy and compress magnetic hemostatic powder 50 containing magnetite against a wound site. The powder 50 may be on the balloon prior to application or applied after the balloon 56 is inflated via a second tube or through an alternative tube. The magnet 58 holds the powder 50 in place so that it can be applied to the wound.

Figure 10:
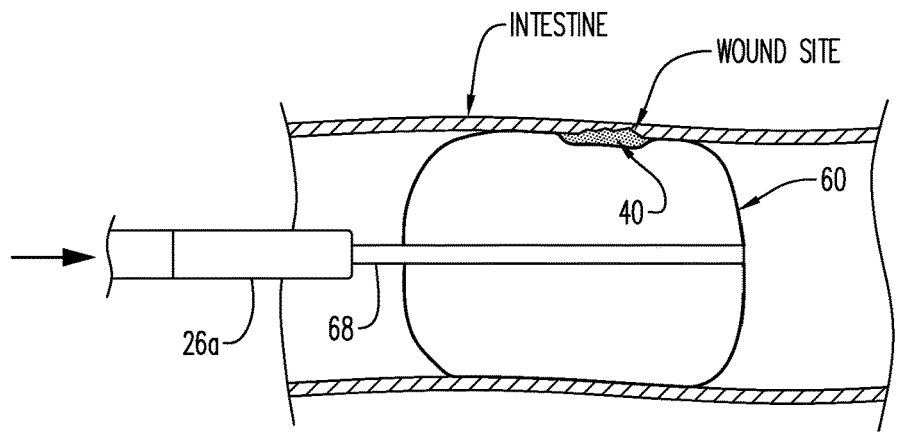
FIG. 10 is a schematic section view of another embodiment of the invention in the form of a large inflatable balloon which has been deployed and then inflated to fill the intestine to apply pressure against a hemostatic powder over the wound site.

In FIG. 10, a large inflatable balloon 60 is deployed through and from the insertion tube 24 and then inflated to fill the intestine to apply pressure against hemostatic powder 40 over the wound site. A magnet may be used in conjunction with the balloon, powder or a solid tablet.

Figure 11:
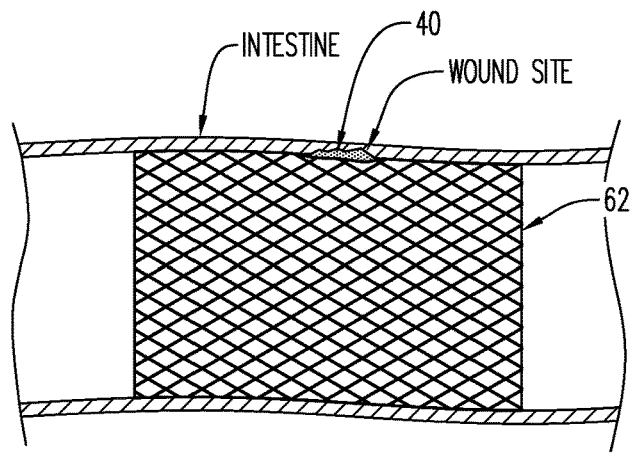
FIG. 11 is a schematic section view showing the deployment of yet another embodiment of the invention in the form of an expandable stent to apply pressure against a hemostatic powder after being applied over the wound site.

FIG. 11 shows an expandable stent 62 which applies pressure against hemostatic powder 40 after being applied and expanded over the wound site. The stent 62 may be biosorbable or removable, and may also be magnetic or a portion thereof to hold and concentrate the powder 40.

Figure 12A:
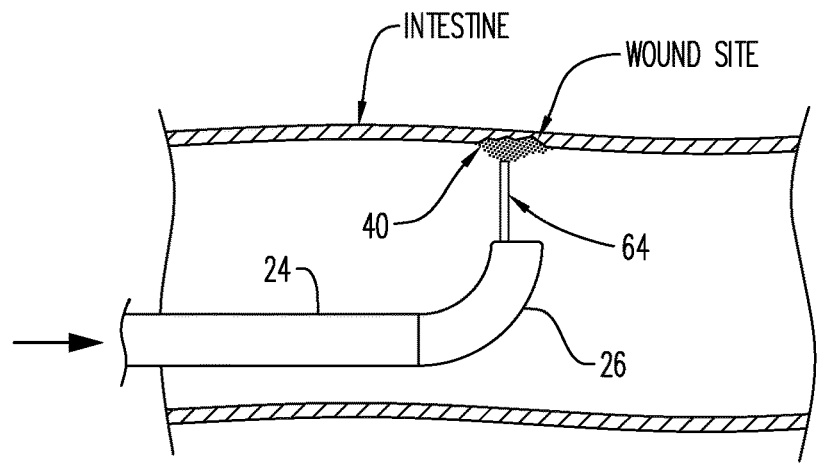
FIGS. 12A and 12B are schematic section views showing the sequential application of a hemostatic powder onto a wound site through a second scope line and then deploying a balloon tamponade through a main line to apply pressure thereagainst.
Figure 12B:
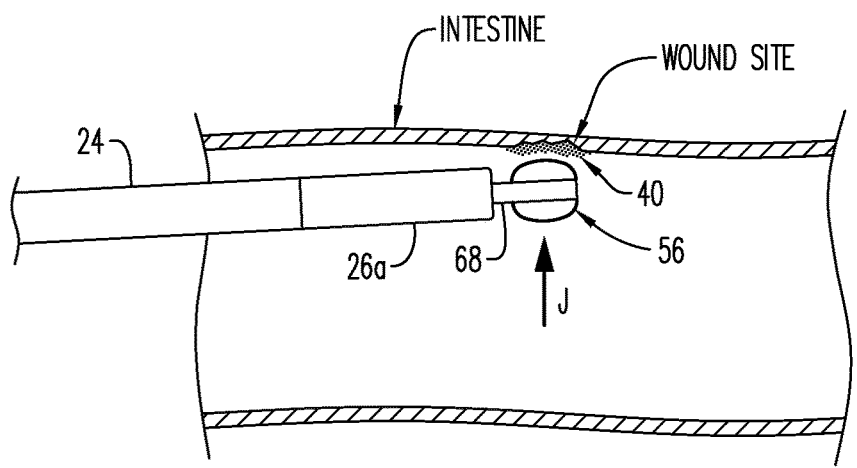
Figure 12C:
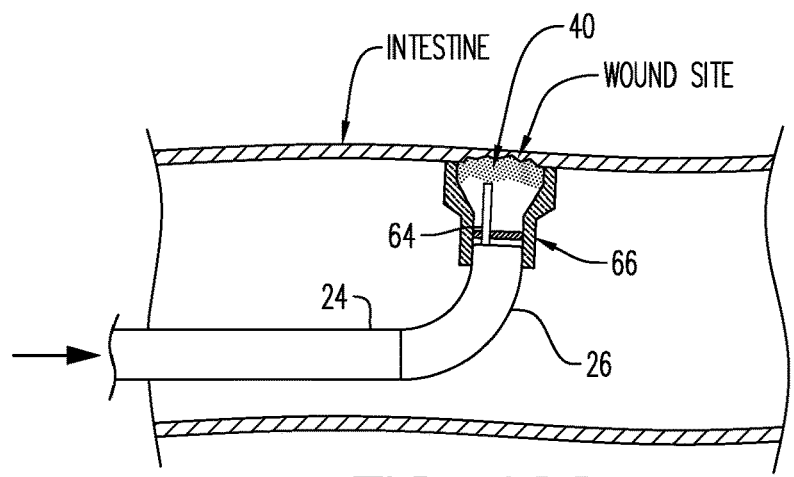
FIGS. 12C and 12D are schematic section views showing the sequential deployment of a hemostatic powder through an application catheter and confined by a clear cap which is also used to apply pressure against the hemostatic powder.
Figure 12D:
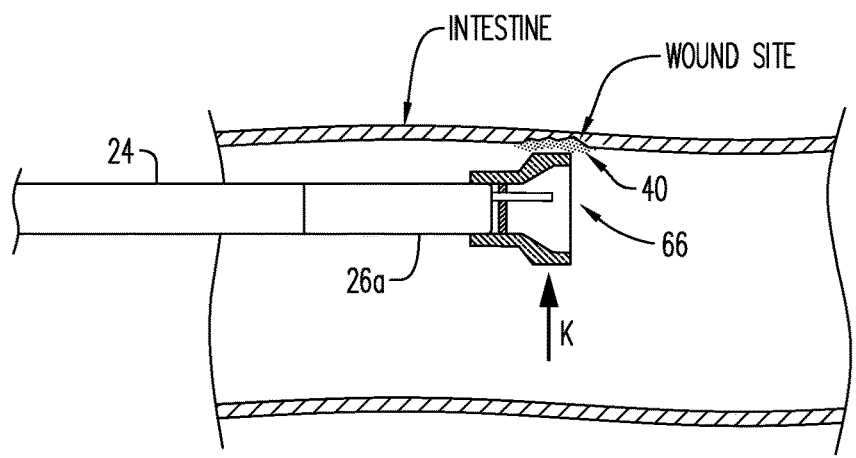

FIGS. 12A and 12B show the sequential application of hemostatic powder 40 onto a wound site through a second application catheter 64, after which the balloon tamponade 56 is deployed through the application catheter 68 after which the bending tip 26 is straightened at 26a and urged in the direction of arrow J to apply pressure against the powder. In FIGS. 12C and 12D, the sequential deployment of hemostatic powder 40 through an application catheter 64 and confinement of the hemostatic powder 40 within a clear cap 66 attached over the end of the bending tip 26 is there shown. The cap 66 is also used to apply pressure against the powder 40 as seen in FIG. 12D by urging the cap 66 in the direction of arrow K after straightening the bending tip 26. The cap 66 may also contain a clear disk through which powder is filled. This disc may act as a plunger as the cap is used to apply pressure.

Figure 13:
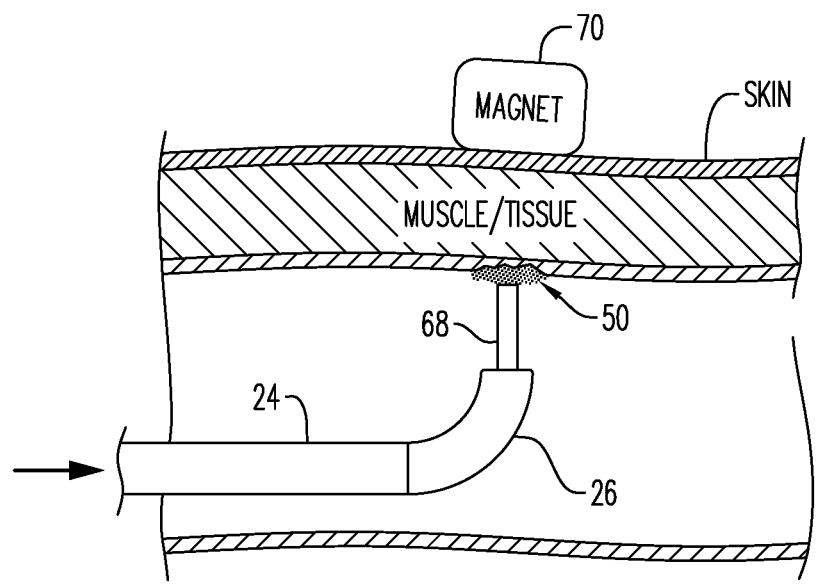
FIG. 13 is a schematic section view showing the hemostatic powder with magnetite being applied over a wound site as facilitated by an external magnet.
Figure 14:
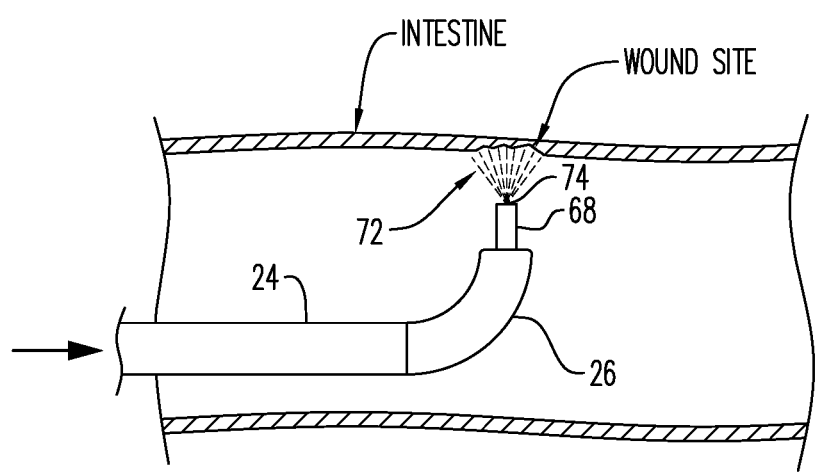
FIG. 14 is a schematic section view showing the application of a ferrate spray solution in the form of $Fe+^3$ against a wound site.

FIG. 13 shows the hemostatic powder with magnetite 50 being applied over a wound site as facilitated by an external magnet 70. In FIG. 14, application of a ferrate spray solution 72 in the form of $Fe+^3$ from a spray nozzle 74 against a wound site is there shown. If sufficient quantity of trivalent salts are applied to blood, it will clot very rapidly. The $Fe+^3$ spray 72 may be any trivalent soluble salt solution, a gel solution containing a soluble trivalent salt, or a bio-derived substance that induces clotting or absorbs blood components. Examples would be a collagen solution/gel, a thrombin containing solution/gel, or a fibrin containing solution/gel. The gel component may be polyvinyl alcohol, gelatin, or the like. The spray 72 may be used in conjunction with any other components in this application, for example, with the clear cap or a balloon funnel. The purpose is to contain, direct and concentrate the spray 72. The spray 72 may be used in conjunction with a gauze or other device for retention and pressure application.

Figure 15A:
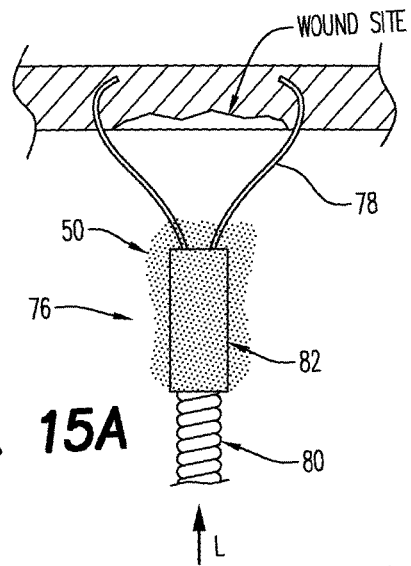
FIGS. 15A, 15B and 15C are schematic section views showing sequential deployment of an endoscopic clip formed of magnetic material which attracts and holds a quantity of hemostatic powder plus magnetite powder magnetically adhered thereto ready for being applied against a wound site as or after the clip is engaged the tissue around the wound site.
Figure 15B:
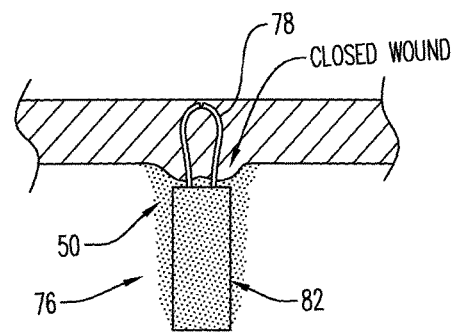

FIGS. 15A and 15B show sequential deployment of an endoscopic clip 76 ("endoclip") formed having a magnetic barrel 82 which attracts and holds a quantity of hemostatic powder with magnetite powder 50 magnetically adhered thereto ready for being applied against a wound site as or after the resilient wire jaws 78 of the endoscopic clip 76 have engaged the tissue around the wound site by urging of an insertion tool 80 in the direction of arrow L. After urging of the wire jaws 78 into the tissue surrounding the wound, the insertion tool is urged in the direction of L' to further set the wire jaws and close the wound. The magnetic hemostatic powder 50 will simultaneously be deposited over the closed wound to effect hemostasis. The magnetic hemostatic powder 50 may be applied to the magnetic barrel 82 prior to use or after deployment of the endoscopic clip 76.

Figure 15C:
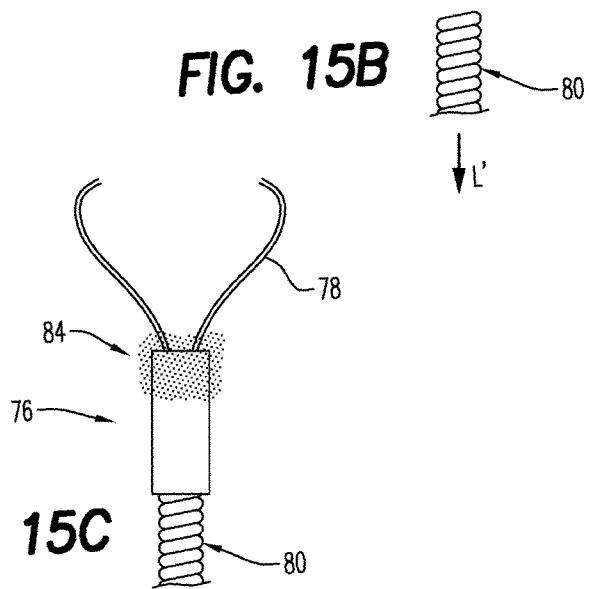

FIG. 15C shows the endoscopic clip containing a styptic powder 84, or a bio-derived substance that induces hemostasis or clot formation. The styptic powder 84 is designed to release after endoscopic clip 76 deployment to assist with hemostasis. The styptic may be a solid or gel.

Figure 16A:
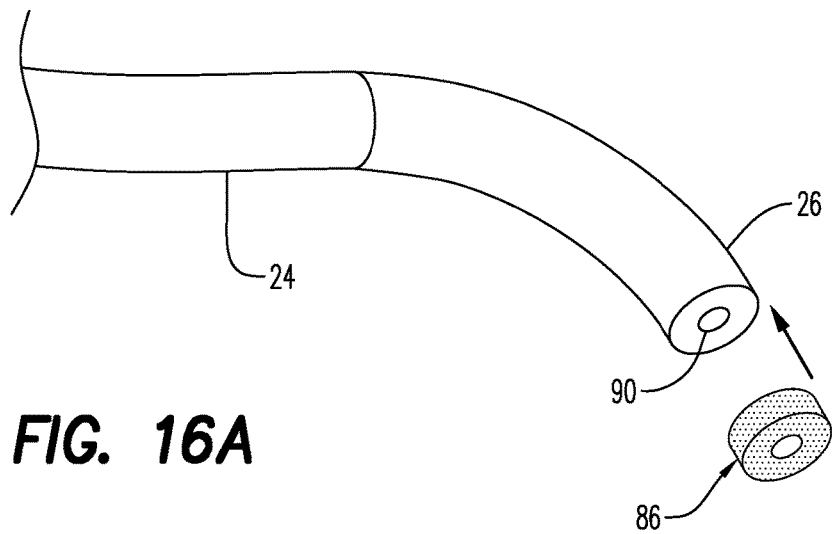
FIGS. 16A and 16B show the sequential application of a hemostatic tablet having a viewing hole formed centrally therethrough for a camera to facilitate accurate positioning of the hemostatic tablet directly over a wound site.
Figure 16B:
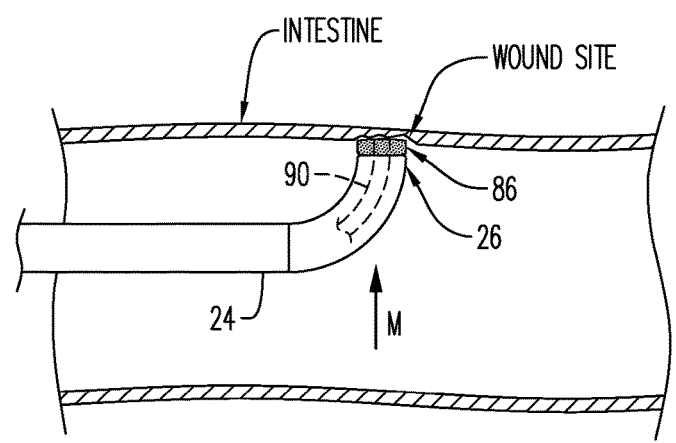

In FIGS. 16A and 16B, the sequential application of a hemostatic tablet 86 having a viewing hole formed centrally therethrough for a camera 90 facilitates accurate positioning of the hemostatic tablet 86 directly over a wound site. A clear disc (not shown) may be used between the scope and the tablet to protect the scope. The camera 90 extends coaxially with the bending tip 26 and with the tablet 86 which is frictionally held in the position shown until deployed in the direction of arrow M. The tablet 86 may be designed to stay whole or break apart upon deployment and may need a protective coating to prevent it from wetting during deployment.

Figure 17A:
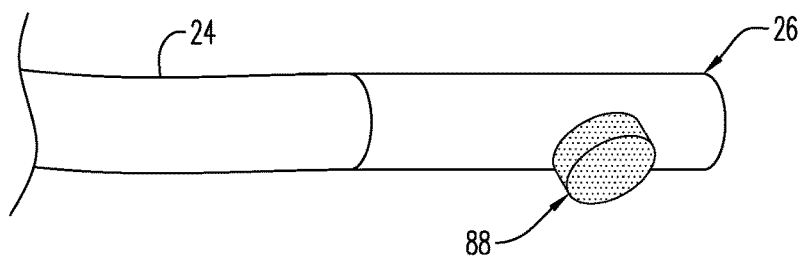
FIGS. 17A and 17B show the sequential application of a hemostatic tablet adhered against the exterior surface of the bending tip to be forcibly applied against the wound site.
Figure 17B:
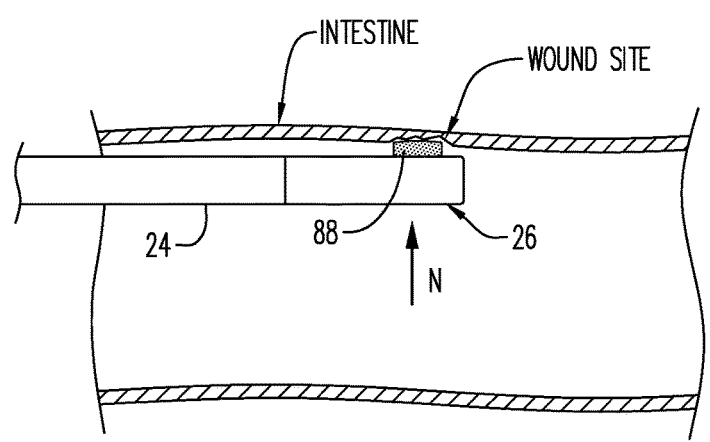

FIGS. 17A and 17B show the sequential deployment of a hemostatic tablet 88 adhered against the exterior surface of the bending tip 26 to be forcibly applied against the wound site in the direction of arrow N. The tablet 88 may need a protective coating to prevent it from wetting during deployment.

Figure 18:
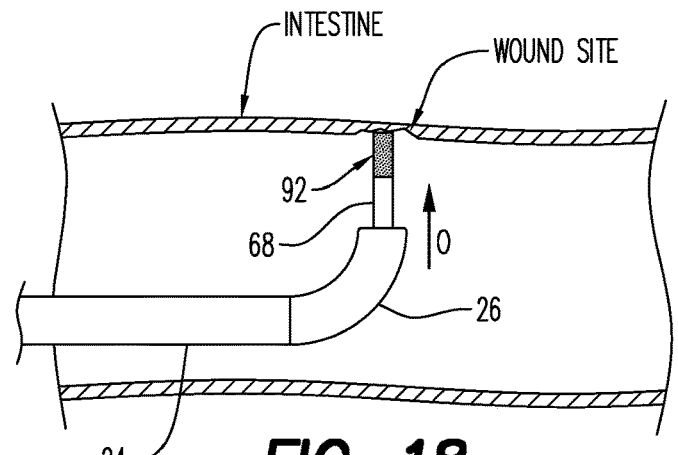
FIG. 18 is a schematic section view showing a hemostatic tablet adhered to the end of a delivery tube being held against a wound site for a time sufficient for adherence of the hemostatic tablet against the wound site.

FIG. 18 is a view showing a hemostatic tablet 92 adhered to the end of the delivery tube 68 and being urged in the direction of O against a wound site for a time sufficient for adherence of the tablet 92 to effect hemostasis against the wound site.

Figure 19:
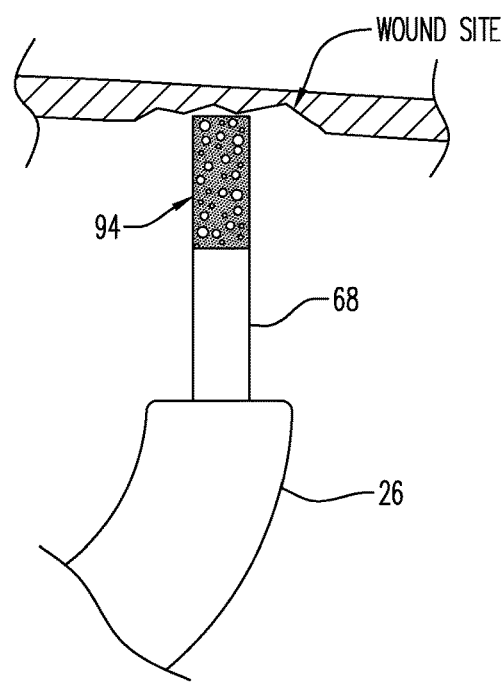
FIG. 19 shows another embodiment of the invention which includes a rapid dissolve substance mixed with a hemostatic powder or tablet that leaves some hemostatic powder behind as it is being held against a wound site.

In FIG. 19, another embodiment includes a rapid-dissolve substance mixed with hemostatic powder to form a tablet 94 that leaves the hemostatic powder behind as it is being held against a wound site. This rapid-dissolve substance may either be a rapidly dissolving component in the tablet or a dissolving coating.

Figure 20:
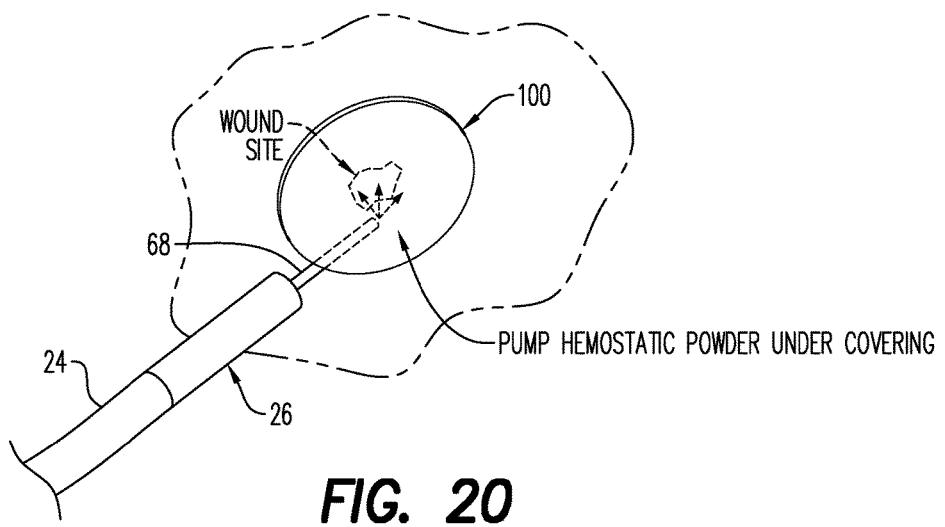
FIG. 20 is a pictorial view of another embodiment of the invention utilizing a delivery tube to pump a hemostatic powder beneath a wound covering placed over a wound site.

FIG. 20 shows a delivery tube 68 pumping hemostatic powder beneath a wound covering 100 placed over a wound site. The covering 100 may also contain an agent to induce or assist with hemostasis or clot formation. Examples would be a trivalent salt solution or solid, thrombin, fibrin, activated cellulose or a combination. The covering 100 is attached to the wound through the interaction of the moisture in the tract, e.g. a PVA coating with an absorptive backing that works similar to a stamp used for postage.

Figure 21:
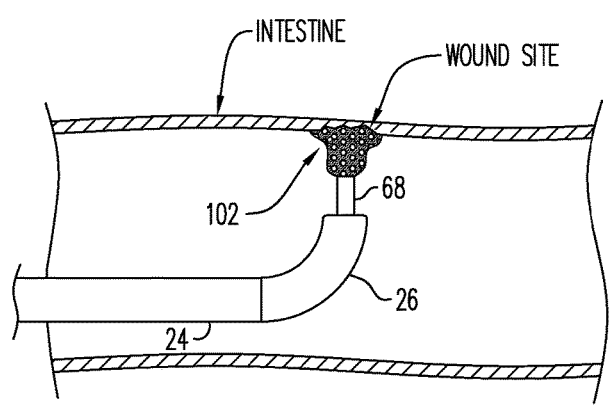
FIG. 21 is a schematic section view showing another embodiment of the invention including the delivery of a quantity of a hemostatic powder plus magnetite mixed with tiny magnets against a wound site.

In FIG. 21, delivery of a quantity of hemostatic powder with magnetite 102 is mixed with tiny magnets against a wound site. The combination of components would form a malleable solid.

Figure 22A:
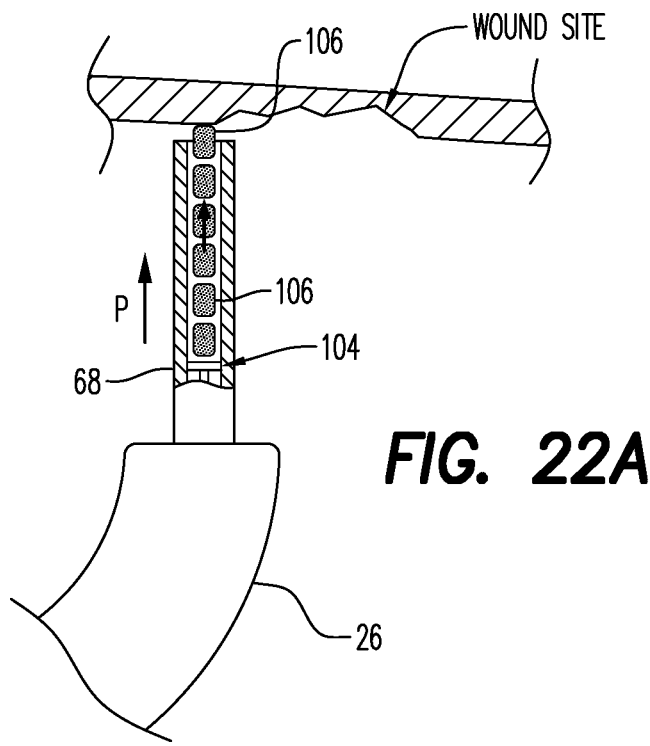
FIGS. 22A and 22B are schematic section views that show the sequential delivery of a plurality of mini hemostatic tablets through a delivery tube, one at a time, as forced to move by a plunger through a delivery tube, the mini hemostatic tablets extending over the wound and being retained in place when the resin plus ferrate reacts with blood in the wound site.
Figure 22B:
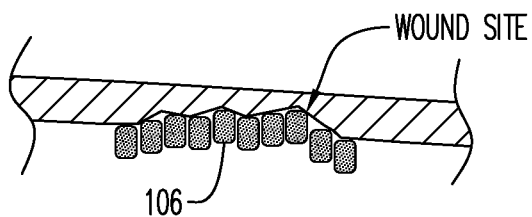

FIGS. 22A and 22B show the sequential delivery of a plurality of mini hemostatic tablets 106 through a delivery tube 68, one at a time in the direction of arrow P, as forced to move by a plunger 104 through the delivery tube 68. The mini hemostatic tablets 106 are deployed to extend over the wound and retained in place by reaction with blood in the wound site. Upon wetting and/or when force is applied to the tablets 106, they may, at least in part, disintegrate into powder.

Figure 23A:
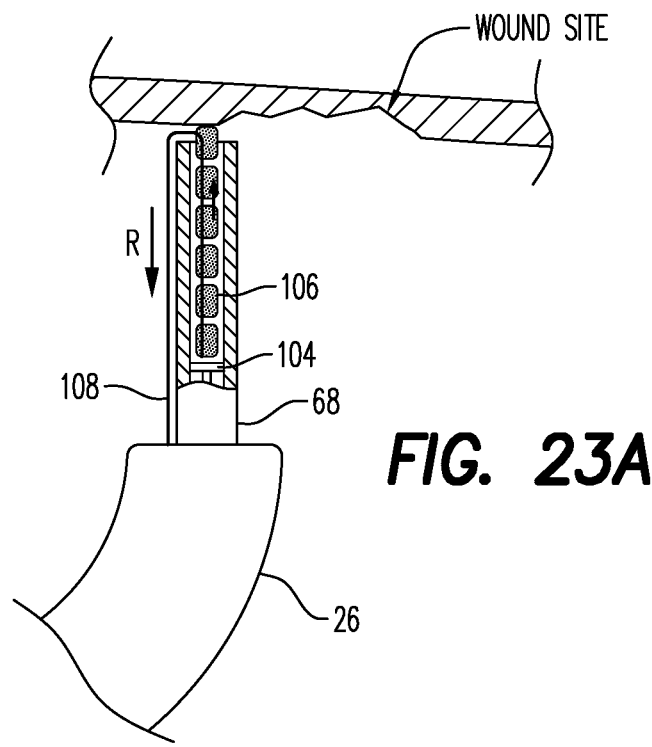
FIGS. 23A and 23B are similar views to FIGS. 22A and 22B except that the mini hemostatic tablets are connected together by a suture which is pulled in the direction of the arrow to deliver each of the mini hemostatic tablets over the wound site one at a time.
Figure 23B:
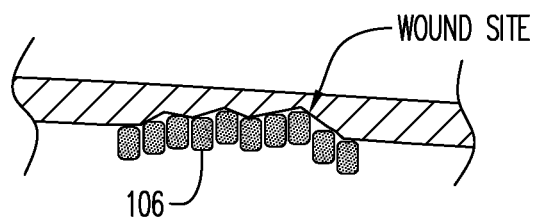

FIGS. 23A and 23B are similar views to FIGS. 22A and 22B except that the mini hemostatic tablets 106 are connected together by a flexible suture 108 which is pulled in the direction of arrow R to deliver each of the mini hemostatic tablets 106 over the wound site, one at a time. The tablets 106 may break away from the suture 108 as indicated into separate tablets, or the tablets may be connected together by a second suture (not shown).

Figure 24A:
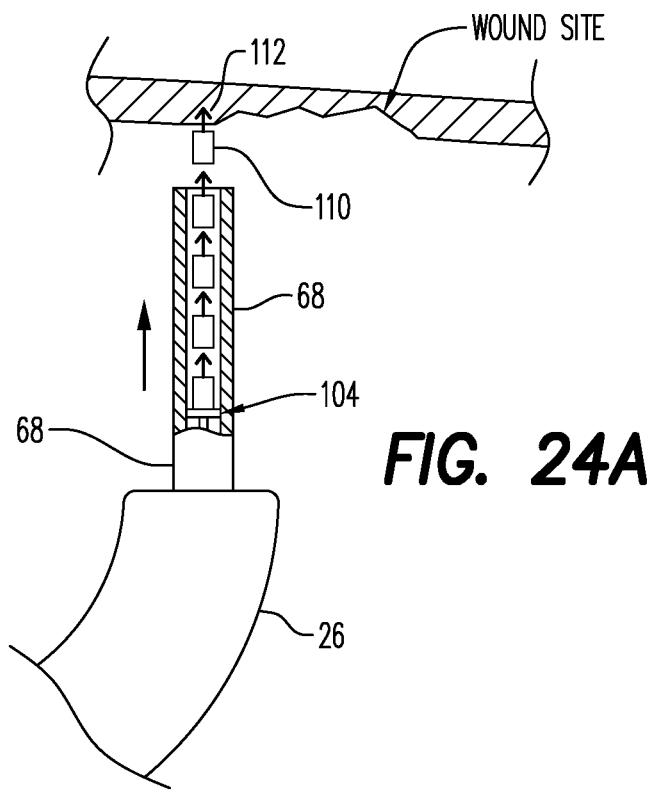
FIGS. 24A and 24B show the deployment of small magnets having barbs disposed on one end which pierce and are retained within the wound site, the magnets being applied by a plunger through a hollow delivery tube, after which a quantity of a hemostatic powder plus is applied over the anchored magnets to hold the powder in place within the wound site.
Figure 24B:
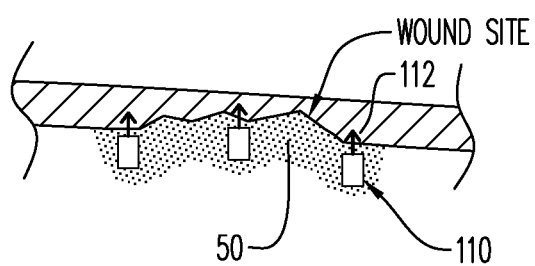

FIGS. 24A and 24B show the sequential deployment of small magnets 110 having end barbs 112 which pierce and are retained within the wound site. The magnets 110 are applied by a plunger 104 through a hollow delivery tube 68, after which a quantity of hemostatic powder with magnetite 50 is applied over the anchored magnets 110 to hold the powder 50 in place within the wound site. As many magnets 110 as are needed may be deployed to completely cover the wound site.

Figure 25A:
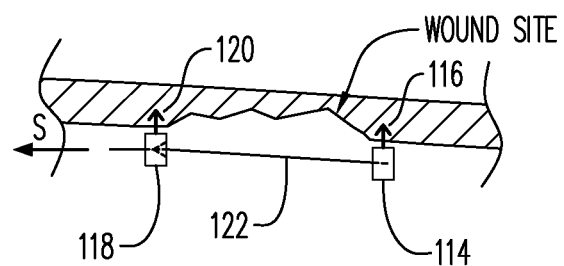
FIGS. 25A and 25B are sequential schematic views showing deployment of barbed anchors opposingly attached across a wound site and a pull suture interengaged between the anchors to pull the anchors together to close the wound.
Figure 25B:
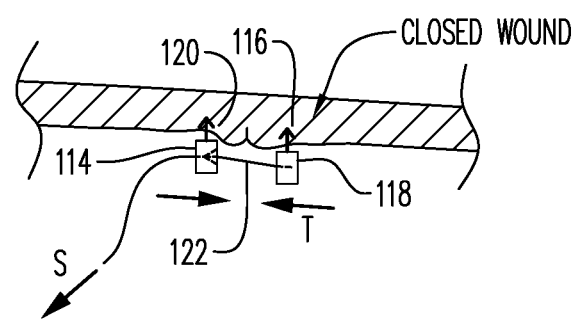

FIGS. 25A and 25B show deployment of barbed anchors 114 and 118 opposingly attached across a wound site and a pull suture 122 interengaged between the anchors 114 and 118 to pull the anchors 114 and 118 together in the direction of arrow S to close the wound. The anchors 114 and 118 may be deployed in pairs and pulled to approximate the wound or several anchors may be deployed. The multi anchor system may have one anchor 114 fixed to the end of the pull suture 122 and every anchor 118 subsequent to the first being a one-way pull type allowing the wound to be slowly approximated in the direction of arrows T-T. The anchors 114 and 118 may be magnetic to allow a magnetic hemostatic powder to be applied and held in place after the anchors are deployed or the anchors may be coated with a styptic or other hemostatic agent.

Figure 26:
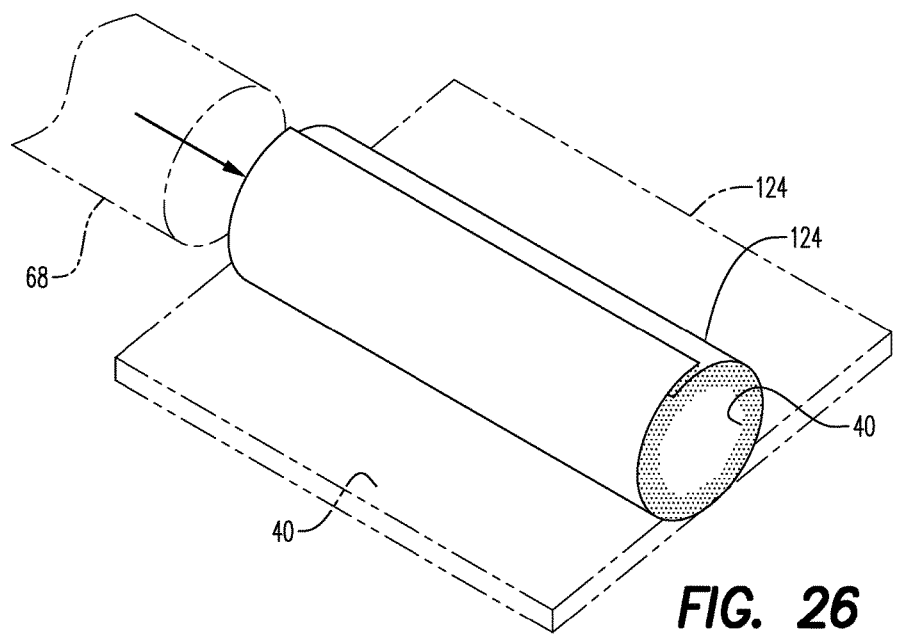
FIG. 26 is a perspective view of another embodiment of the invention including a coiled hemostatic powder-coated sheet which uncoils when deployed from a hollow delivery tube after which it is positioned against the wound site.

In FIG. 26, a coiled hemostatic powder-coated sheet 124 uncoils when deployed from the hollow delivery tube 68, after which it is positionable against the wound site. The sheet 124 may be coiled with the hemostatic agent 40 on either side thereof. A sheath may be necessary to protect the hemostatic powder 46.

Figure 27A:
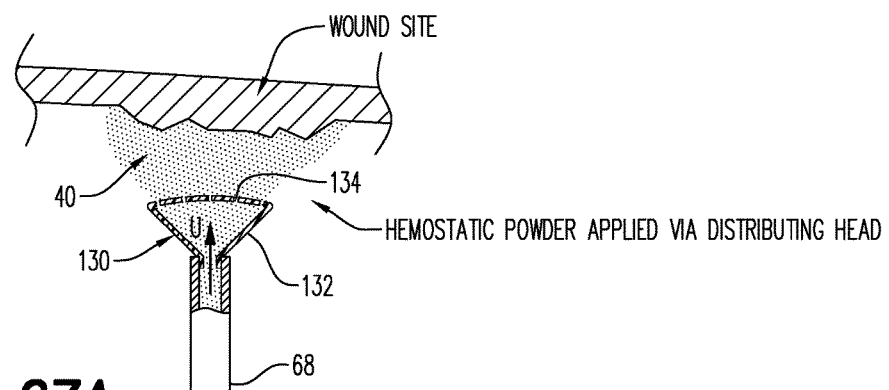
FIGS. 27A and 27B are schematic section views showing the deployment of a hemostatic powder through a hollow expandable distributing head having apertures formed along its outwardly facing surface, the hemostatic powder being distributed over the wound site, after which the distributing head is then utilized in FIG. 26B to tamp the hemostatic powder into place over the wound site.
Figure 27B:
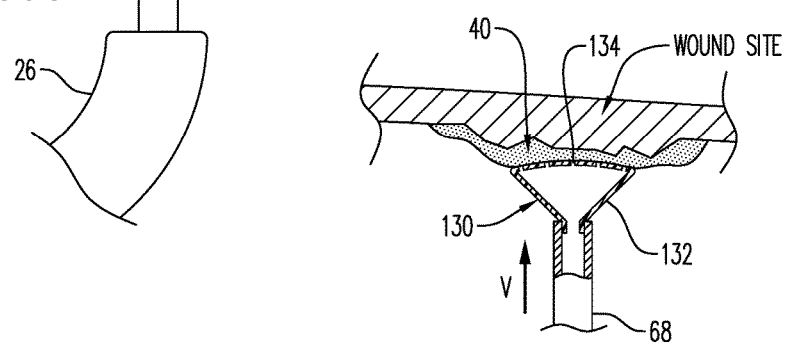

FIGS. 27A and 27B show the deployment of hemostatic powder 40 through a hollow expandable distributing head assembly 130 having apertures 134 formed along its outwardly facing surface, the powder 40 being distributed through apertures 134 in the direction of arrow U over the wound site, after which the distributing head 132 is then utilized in FIG. 26B to tamp the powder 40 in the direction of arrow V into place over the wound site.

Figure 28A:
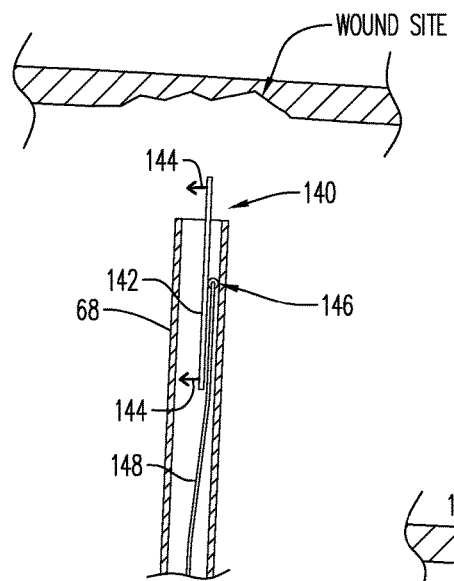
FIGS. 28A, 28B and 28C are sequential schematic section views of the deployment of an end-barbed spring clip which engages into the edges of the wound site to be drawn together to close the wound as a pull wire is drawn into the delivery tube as the clip spring is arcuately formed.
Figure 28B:
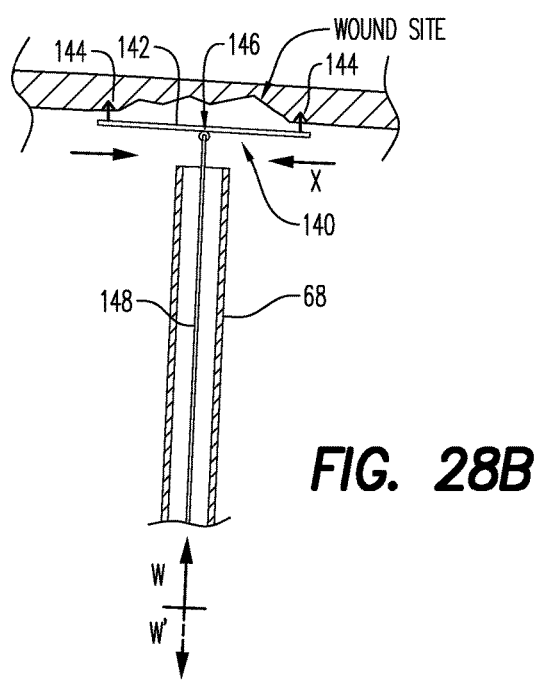
Figure 28C:
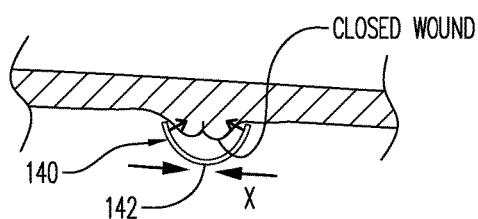

FIGS. 28A, 28B and 28C are sequential views of the deployment of spring wire clip 140 having barbs 144 at each end of a spring wire 142 which engage into tissue at the edges of the wound site when push/pull wire 148 is extended in the direction of arrow W. As the spring wire clip 140 is deployed from the application catheter 68 by pushing the push/pull wire 148 in the direction of arrow W, the spring wire pivots about pivot anchor 146 as seen in FIG. 28B. After the barbs 144 are set, they are drawn together in the direction of arrow X to close the wound as the push/pull wire 148 is drawn in the direction of arrow W' into the delivery tube as the spring wire 142 is arcuately formed to close the wound. The clip 140 may also be constructed of a material that retains shape, like titanium, and when pulled, it springs back from a straight wire into a loop. This clip would be much smaller than other endoclips currently marketed.

FIGS. 29 to 34 show a number of embodiments for delivering the hemostatic powder 40 or hemostatic pellets through the application catheter 68. In FIG. 29, the plunger 104 is utilized to push the hemostatic powder 40 while in FIG. 30, gas under pressure forces the hemostatic powder 40 to discharge from the application catheter 68. In FIG. 31, a venturi 68a is utilized to draw the hemostatic powder 40 or 50 into the venturi 68a for discharge under gas pressure from the end of the application catheter 68. FIG. 32 shows a drill auger 152 utilized to force the hemostatic powder 40 or hemostatic pellets out through the application catheter 68. FIG. 33, shows the utilization of an outer auger 154 to force the hemostatic powder 40 or hemostatic pellets through a central feed passage 156 and outwardly from the application catheter 68. FIG. 34 discloses a wire auger 158 for the same purpose.

While a number of exemplary aspects and embodiments have been discussed above, those of skill in the art will recognize certain modifications, permutations and additions and subcombinations thereof. It is therefore intended that the following appended claims and claims hereinafter introduced are interpreted to include all such modifications, permutations, additions and subcombinations that are within their true spirit and scope.

The invention claimed is:

1. A method of arresting blood flow from a bleeding wound produced within the alimentary canal of a living organism accessible only from a natural body orifice by endoscopic surgery consisting of the steps of:
   inserting an endoscopic instrument into the living organism through the natural body orifice;
   inserting a retaining device through the endoscopic instrument and positioning said retaining device in close proximity over the bleeding wound;
   displacing a hemostatic substance through the endoscopic instrument into contact with said retaining device and against the wound;
   said hemostatic substance consisting of a resin/ferrate or hydrogen resin in powder or tablet form;
   retaining and encompassing said hemostatic substance against the bleeding wound through the use of said retaining device for preventing the blood excreted by the bleeding wound from displacing the hemostatic substance throughout the alimentary canal;
   maintaining said hemostatic substance against the blood excreted by the bleeding wound through the use of said retaining device for a time sufficient for said hemostatic substance in contact with the blood to form a scab comprised of dried blood and said hemostatic substance as a result of contacting the blood excreted by the bleeding wound; and
   removing the endoscopic instrument from the living organism while leaving behind said the scab attached over the wound for subsequent discharge from the body through the natural orifice.

2. The method of arresting blood flow from the bleeding wound as set forth in claim 1, further including the step of withdrawing said retaining device from against said scab and leaving behind said scab attached over the wound.

3. A hemostatic scab for arresting blood flow from a bleeding wound produced within the alimentary canal of a living organism accessible only from a natural body orifice by endoscopic surgery formed by the process of:
   inserting an endoscopic instrument into the living organism through the natural body orifice;
   inserting a retaining device through the endoscopic instrument and positioning said retaining device in close proximity over the bleeding wound;
   displacing a hemostatic substance through the endoscopic instrument into contact with said retaining device and against the bleeding wound;
   said hemostatic substance consisting of a resin/ferrate or hydrogen resin in powder or tablet form;
   retaining and encompassing said hemostatic substance against the bleeding wound through the use of said retaining device for preventing the blood excreted by the bleeding wound from displacing the hemostatic substance throughout the alimentary canal;
   maintaining said hemostatic substance against the blood excreted by the bleeding wound through the use of said retaining device for a time sufficient for said hemostatic substance in contact with the blood to form a scab comprised of dried blood and said hemostatic substance as a result of contacting the blood excreted by the bleeding wound; and
   removing the endoscopic instrument from the living organism while leaving behind said the scab attached over the wound for subsequent discharge from the body through the natural orifice.

4. A method of arresting blood flow from a bleeding wound produced within the alimentary canal of a living organism accessible only from a natural body orifice by endoscopic surgery comprising the steps of:
   inserting an endoscopic instrument into the living organism through the natural body orifice;
   said endoscopic instrument having an endoscopic bore;
   inserting a retaining device into and through said endoscopic bore of said endoscopic instrument and positioning said retaining device in close proximity over the bleeding wound;
   said retaining device having a retaining device bore;

displacing a hemostatic substance into and through said retaining device bore of said retaining device and against the bleeding wound;

said hemostatic substance including a resin/ferrate or hydrogen resin in powder or tablet form;

retaining and encompassing said hemostatic substance against the bleeding wound through the use of said retaining device for preventing the blood excreted by the bleeding wound from displacing the hemostatic substance throughout the alimentary canal;

maintaining said hemostatic substance against the blood excreted by the bleeding wound through the use of said retaining device for a time sufficient for said hemostatic substance in contact with the blood to form a scab comprised of dried blood and said hemostatic substance as a result of contacting the blood excreted by the bleeding wound; and removing the endoscopic instrument from the living organism while leaving behind said the scab attached over the wound for subsequent discharge from the body through the natural orifice.

5. The method of arresting blood flow from the bleeding wound as set forth in claim 4, further including the step of retracting said retaining device relative to said endoscopic bore of said endoscopic instrument for positioning said retaining device remotely from the bleeding wound.

* * * * *